(12) United States Patent
Rausch et al.

(10) Patent No.: US 6,538,082 B2
(45) Date of Patent: Mar. 25, 2003

(54) ASYMMETRIC SILICON-BRIDGED METALLOCENES USEFUL AS CATALYSTS IN THE POLYMERIZATION OF α-OLEFINS, PROCESS FOR THEIR PREPARATION AND USE OF SAID METALLOCENES FOR THE POLYMERIZATION OF α-OLEFINS

(75) Inventors: Marvun D. Rausch, Amherst, MA (US); Emma J. Thomas, Amherst, MA (US); Serge Bettonville, Crisnée (BE)

(73) Assignee: Solvay Polyolefins Europe-Belgium, Brussels (BE)

( * ) Notice: Subject to any disclaimer, the term of this patent is extended or adjusted under 35 U.S.C. 154(b) by 0 days.

(21) Appl. No.: 09/729,099

(22) Filed: Dec. 5, 2000

(65) Prior Publication Data

US 2002/0103312 A1 Aug. 1, 2002

(51) Int. Cl.[7] .................................................. C08F 4/72
(52) U.S. Cl. ...................... 526/170; 526/160; 526/943; 526/351; 526/352; 556/11
(58) Field of Search .......................... 556/11; 502/117, 502/103; 526/160, 170, 943, 351, 352

(56) References Cited

U.S. PATENT DOCUMENTS

| | | | | |
|---|---|---|---|---|
| 5,453,410 A | * | 9/1995 | Kolthammer et al. | 502/155 |
| 5,670,680 A | * | 9/1997 | Newman et al. | 556/53 |
| 5,814,714 A | * | 9/1998 | Palomo et al. | 526/336 |
| 6,004,897 A | * | 12/1999 | Imuta et al. | 502/103 |
| 6,100,416 A | * | 8/2000 | Rasuch et al. | 556/53 |
| 6,355,747 B1 | * | 3/2002 | Rausch et al. | 526/160 |

FOREIGN PATENT DOCUMENTS

| | | |
|---|---|---|
| EP | 0754698 A2 | 1/1997 |
| WO | WO 95/27717 | 10/1995 |

OTHER PUBLICATIONS

Thomas, E. J.; Rausch, M. D.; Chien, J. C. W. Organometallics 2000, 19, 4077.*
Thomas, E. J.; Rausch, M. D.; Chien, J. C. W. Organometallics 2000, 19, 5744.*
Obora, Y.; Stern, C. L.; Marks, T. J.; Nickias, P. N. Organometallics 1997, 16, 2503.*
Thomas, E. J.; Rausch, M. D.; Chien, J. C. W. Macromolecules 2000, 33, 1546.*
Thomas, E. J.; Rausch, M. D.; Chien, J. C. W. Organometallics 1999, 18, 1439.*
Leino, R.; Luttikhedde, H. J. G. ; Lehtonen, A. ; Wilén, C.–E.; Näsman, J. H. J. Organomet. Chem. 1997, 545–546, 219.*
Rieger, B.; Jany, G. Chem. Ber. 1994, 127, 2417.*
Macromolecules, 2000, 33, 1546–1552.
Journal of Organometallic Chemistry, 1997, 545–546, 219–224.

\* cited by examiner

Primary Examiner—David W. Wu
Assistant Examiner—Rip A. Lee
(74) Attorney, Agent, or Firm—Venable, LLP; Marina V. Schneller

(57) ABSTRACT

Novel asymmetric silicon-bridged metallocenes useful as catalysts in the polymerization of olefins and process for preparing said metallocenes.

The novel metallocenes are represented by the general formula (I):

$$(SiR'R'')(C_p)(C_{p'})MXX' \qquad (I)$$

wherein $C_p$ is a partially or fully hydrogenated fluorenyl moiety selected from those of formula (II) and (III)

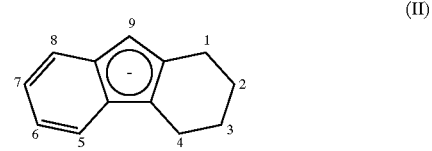

(II)

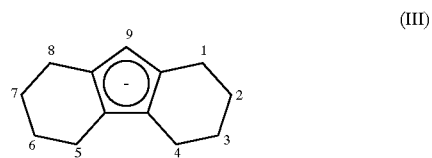

(III)

$C_{p'}$ is an indenyl group selected from those of formula (IV)

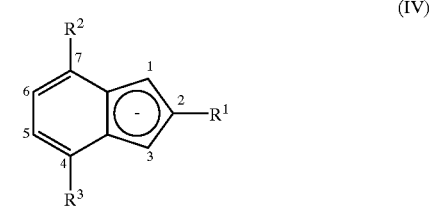

(IV)

M represents a transition metal selected from Ti, Zr and Hf,
X and X' represent, same or different from each other, a halogen atom,
$R^1$, $R^2$ and $R^3$ are, same or different from each other, an alkyl group containing 1 or 2 carbon atoms, an aryl group containing from 6 to 10 carbon atoms or a hydrogen atom,
$(SiR'R'')$ is a divalent group which bridges the two groups $C_p$ and $C_{p'}$ repectively on position 9 and 1,
R' and R'' are, same or different from each other, an alkyl or aryl group containing from 1 to 10 carbon atoms.

Process for producing said metallocenes and process for the polymerization of α-olefins such as ethylene and propylene by means of said metallocenes.

6 Claims, No Drawings

ASYMMETRIC SILICON-BRIDGED METALLOCENES USEFUL AS CATALYSTS IN THE POLYMERIZATION OF α-OLEFINS, PROCESS FOR THEIR PREPARATION AND USE OF SAID METALLOCENES FOR THE POLYMERIZATION OF α-OLEFINS

TECHNICAL FIELD

The present invention relates to novel asymmetric silicon-bridged metallocenes useful as catalysts for the polymerization of α-olefins. It relates more specifically to novel silicon-bridged metallocenes containing an indenyl and a partially or fully hydrogenated fluorenyl moiety and to a process for their preparation. Finally it relates to a process for polymerization of α-olefins by using said asymmetric silicon-bridged metallocenes.

BACKGROUND OF THE INVENTION

Some asymmetric silicon-bridged metallocenes derived from group 4 metals and containing fluorenyl and indenyl moieties have already been proposed for the polymerization of α-olefins such as ethylene and propylene. For example, the use of silicon-bridged (9-fluorenyl)-(1-substituted indenyl) zirconium dichlorides in combination with aluminoxanes for the polymerization of α-olefins is disclosed in EP-A-0 754 698 and Macromolecules, 2000, 33 (5), 1546. However, the productivity and stability of such metallocenes remain insufficient.

Symmetric silicon-bridged bis(octahydrofluorenyl) zirconocenes and their use as catalysts for the polymerization of ethylene have been reported by Näsman et al. (J. Organomet. Chem., 1997, 545, 219) and are decribed in WO 95/27717. The latter also discloses the use of symmetric silicon-bridged bis(tetrahydrofluorenyl)zirconocenes. However, these zirconocenes are not suitable for the production of isotactic polypropylene.

Accordingly, there is still a need for silicon-bridged metallocene catalysts containing indenyl and fluorenyl moieties yielding very stereoregular polypropylene with high catalytic activity.

SUMMARY OF THE INVENTION

It is an object of the present invention to solve the above-mentioned problems by providing novel stable metallocenes useful as catalysts for α-olefin polymerization which are, in particular, able to produce, with a particularly high activity, polyethylene and highly stereoregular polypropylene and a process for preparing such metallocenes. It is another object of the present invention to provide a process for polymerization of the α-olefins by means of said metallocenes.

The invention is thus related to novel asymmetric silicon-bridged metallocenes of formula (I):

$$(SiR'R'')(C_p)(C_{p'})MXX' \qquad (I)$$

wherein $C_p$ is a partially or fully hydrogenated fluorenyl moiety selected from those of formula (II) and (III)

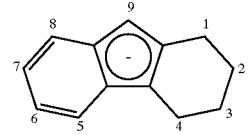

(II)

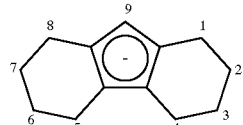

(III)

$C_{p'}$ is an indenyl group selected from those of formula (IV)

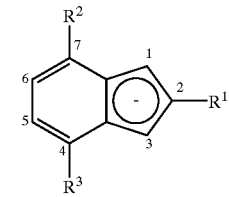

(IV)

M represents a transition metal selected from Ti, Zr and Hf,
X and X' represent, same or different from each other, a halogen atom,
$R^1$, $R^2$ and $R^3$ are, same or different from each other, an alkyl group containing 1 or 2 carbon atoms, an aryl group containing from 6 to 10 carbon atoms or a hydrogen atom,
(SiR'R'') is a divalent group which bridges the two groups $C_p$ and $C_{p'}$ repectively on position 9 and 1,
R' and R'' are, same or different from each other, an alkyl or aryl group containing from 1 to 10 carbon atoms.

The invention also relates to a process for the preparation of these metallocenes.

Metallocenes of formula (I) wherein $C_p$ is a tetrahydrofluorenyl group selected from those of formula (II) are preferably prepared by a route comprising the following steps:

a) production of 9-(1,2,3,4-tetrahydrofluorenyl)-1-(indenyl (or substituted indenyl))-dialkyl(or diaryl)silane from the (indenyl (or substituted indenyl))-dialkyl(or diaryl)-chlorosilane and 1,2,3,4-tetrahydrofluorenyllithium, b) production of the dilithium salt of 9-(1,2,3,4-tetrahydrofluorenyl) (1-indenyl (or substituted indenyl))-dialkyl(or diaryl)silane precursor and c) production of the metallocene by reacting the said dilithium salt with a halide of one of the transition metals mentioned hereabove.

Metallocenes of formula (I) wherein Cp is an octahydrofluorenyl group of formula (III) are preferably prepared by a route comprising the following steps:

a') production of 9-(1,2,3,4,5,6,7,8-octahydrofluorenyl)-1-(indenyl (or substituted indenyl))-dialkyl(or diaryl)silane from (indenyl (or substituted indenyl))lithium and 9-(1,2,3,4,5,6,7,8-octahydrofluorenyl) dichloro-dialkyl (or diaryl)silane, b') production of the dilithium salt of 9-(1,2,3,4,5,6,7,8-octahydrofluorenyl)-1-(indenyl (or substituted indenyl))-dialkyl(or diaryl)silane precursor and c') production of the metallocene by reacting the said dilithium salt with a halide of one of the transition metals mentioned hereabove.

Finally the present invention relates to a process for polymerization of α-olefins by means of said metallocenes.

DETAILED DESCRIPTION

According to a first aspect, the present invention relates to novel stable metallocenes of the above general formula (I).

Preferably the transition metal is selected from hafnium and zirconium. Most preferably the transition metal is zirconium.

The halogen atoms X and X' are preferably chlorine or bromine atoms and most preferably they are both chlorine atoms.

The group $R^1$ represents preferably a methyl group.

The groups $R^2$ and $R^3$ represent preferably a methyl group, an aryl group containing from 6 to 10 carbon atoms or a hydrogen atom, with at least one of $R^2$ or $R^3$ being different from hydrogen. Most preferably $R^2$ is a hydrogen atom and $R^3$ is a phenyl group.

The groups R' and R" are preferably alkyl groups and more particularly alkyl groups containing from 1 to 3 carbon atoms. Most preferably R' and R" are a methyl group.

Among the most preferred metallocenes according to the present invention belongs the dimethylsilylene-[η5-1-(2-methyl-4-phenyl)indenyl]-[η5-9-(1,2,3,4,5,6,7,8-octahydrofluorenyl)] zirconium dichloride. Another example of most preferred metallocenes according to the present invention is the dimethylsilylene-[η5-1-(2-methyl-4-phenyl)indenyl]-[η5-9-(1,2,3,4-tetrahydrofluorenyl)] zirconium dichloride.

When used in combination with a cocatalyst, such as for example aluminoxane, said novel stable metallocenes are able to produce with a high activity polyethylene and highly stereoregular polypropylene.

According to a second aspect, the present invention relates to a process for producing the novel metallocenes of general formula (I) as described hereabove.

Preferably, step (a) is carried out by reacting the 1,2,3,4-tetrahydrofluorenyllithium with the chlorosilane in equimolar quantity.

Preferably, step (b) is carried out with at least two molar equivalents of butyllithium per mole of the 9-(1,2,3,4-tetrahydrofluorenyl)-1-(indenyl (or substituted indenyl))-dialkyl(or diaryl)-silane precursor, followed by reacting the obtained dilithium salt with one equivalent of transition metal halide.

Preferably, the step (a) is carried out in an inert solvent such as diethylether or a mixture of these, most often at about 0° C. At the end of the reaction, the suspension is usually hydrolyzed and the organic phase is isolated. After removal of the solvent, the 9-(1,2,3,4-tetrahydrofluorenyl)-1-(indenyl (or substituted indenyl))-dialkyl(or diaryl)-silane precursor is isolated.

Preferably, step (b) is carried out in an inert solvent, such as diethylether, hexane, pentane or tetrahydrofuran (THF) often at 0° C. The resulting lithium salt is advantageously separated from the solvent and washed prior to being reacted, in step (c), with about one equivalent of a transition metal halide selected from halides of Ti, Zr and Hf.

Step (c) is preferably carried out in an inert solvent, such as an ether, often at 0° C. After removal of the solvent, the solid metallocene of formula (I) wherein $C_p$ is a group selected from those of formula (II) is isolated as a mixture of isomers.

Preferably, steps (a'), (b') and (c') are carried out in the same way as respectively the preferred steps (a), (b) and (c) for metallocenes of formula (I) wherein Cp is a group selected from those of formula (II). The 9-(1,2,3,4,5,6,7,8-octahydrofluorenyl)chloro-dialkyl(or diaryl)silane is generally synthesized as described in Organometallics, 1997, 16, 2503.

The novel metallocenes according to the present invention are useful as catalysts for the polymerization of α-olefins. The reaction is carried out by contacting said α-olefins with the said metallocene under polymerization conditions. It can be carried out in solution or in suspension in a hydrocarbon diluent or in suspension in one of the monomers maintained in the liquid form or in the gas phase. The polymerization conditions are well known by persons skilled in the art.

The metallocenes according to the invention can be used in combination with each other. They can also be used in combination with aluminoxanes. Methylaluminoxane (MAO) is preferred. They can also be used in combination with an ionizing agent. This ionizing agent can be chosen from the compounds comprising a first part which has the properties of a Lewis acid and which is capable of ionizing the metallocene and a second part that is inert towards the ionized metallocene. Examples of ionizing agents are triphenylcarbenium tetrakis(pentafluorophenyl) borate, N,N'-dimethylanilinium tetrakis(pentafluorophenyl) borate, tri(n-butyl)ammonium tetrakis(pentafluorophenyl)borate, tri (pentafluorophenyl)boron, triphenylboron, trimethylboron, tri(trimethylsilyl)borate and organoboroxines.

Organometallic compounds are generally used as cocatalysts and/or poison scavengers. They can be selected from organometallic compounds of lithium, magnesium, zinc, aluminium or tin. The best results are obtained with organoaluminium compounds and in particular with trialkylaluminium compounds.

The α-olefins can be chosen from those containing up to 20, preferably up to 12 carbon atoms per molecule. The α-olefin is preferably ethylene or propylene. The metallocenes according to the present invention may be used for the homopolymerization of one of these α-olefins or for the copolymerization-random or block copolymerization-of one of these α-olefins with one or more comonomers. The preferred comonomers of ethylene are butene, hexene and their mixtures. The preferred comonomers of propylene are ethylene, butene and their mixtures.

The novel metallocenes according to the invention are stable molecules and are especially well adapted to polymerize with a particularly high activity ethylene and propylene, and are able to produce highly stereoregular polypropylene.

In addition to the foregoing description of the invention, the following examples are provided to illustrate the present invention.

In these examples reactions are carried out under an argon atmosphere using standard Schlenk techniques. Diethyl ether, THF, hexane and pentane were distilled from Na/K alloy under argon. Dichloromethane was distilled from $CaH_2$ under argon. MAO was purchased as a solution in toluene from Akzo Nobel and used as received. All other reagents were purchased from Aldrich and used without further purification.

Melting points (Tm) of the polymers were determined by DSC with a Perkin-Elmer DSC-System. $^{13}C$ NMR spectra for pentad (mmmm in mol %) analysis were determined on an AMX500 spectrometer at 90° C. in $C_6H_3Cl_3$ with $C_6D_6$. Triad (mm in mol %) analysis was performed on $^{13}C$ NMR spectra recorded on an AC-200 spectrometer at 120° C. in $C_6H_3Cl_3$. $^1H$ NMR spectra were recorded on a AC-200 spectrometer at room temperature in $CDCl_3$. Molecular masses were determined by High Resolution Mass Spectrometry (HRMS). The molecular weight (Mw) and molecular weight distribution (Mw/Mn) of the polymers were determined by gel permeation chromatography (GPC-150C apparatus manufactured by Waters Co Ltd) recorded at 135° C. using a trichlorobenzene solution having a polymer concentration of 0.5 g/l and a polystyrene gel column, e.g. Waters Styragel HMW 6E available from Waters Co. Ltd.

1. Preparation of Metallocenes

EXAMPLE 1

Preparation of the Dimethylsilylene-[$\eta^5$-1-(2-methyl-4-phenyl)indenyl]-[$\eta^5$-9-(1,2,3,4-Tetrahydrofluorenyl)] Zirconium Dichloride (Catalyst 1)

a) Production of [1-(2-methyl-4-phenyl)indenyl]-[-9-(1,2,3,4-tetrahydrofluorenyl)]dimethylsilane To a solution of 2.00 g (9.7 mmol) of 2-methyl-7-phenylindene in 40 ml of dry diethyl ether at 0° C. was added dropwise a 1.6 M solution of butyllithium in hexane (6.06 ml, 9.7 mmol). The solution was stirred at room temperature for 5 h. The solvent was removed under vacuum and the residue was washed twice with 20 ml of dry pentane. The anion was dried under vacuum, dissolved in 40 ml of dry diethyl ether and 5 ml dry THF, and then added dropwise via cannula to 2.36 ml (19.4 mmol) dichlorodimethylsilane in 20 ml of dry diethyl ether at 20° C. The addition was carried out over a 1 h period and the suspension was then stirred for 1 h at room temperature. The solvents and excess dichlorodimethylsilane were then removed under vacuum. The resulting oil was suspended in 30 ml of dry diethyl ether at 0° C. To this was added dropwise by cannula, one equivalent of 1,2,3,4-tetrahydrofluorenyllithium, prepared from 1.65 g (9.7 mmol) of 1,2,3,4-tetrahydrofluorene (prepared according to the method described by Colonge et al., Bull. Chim. Soc. Fr., 1953,75) and 6.06 ml (9.7 mmol) of butyllithium in 30 ml of dry ether and 10 ml of dry tetrahydrofuran. The suspension was allowed to stir overnight at room temperature and hydrolyzed with aqueous NH$_4$Cl. The organic phase was separated and the aqueous layer was extracted with ether. The combined organic phases were dried (MgSO$_4$), filtered and the solvent was removed. The oily residue was recrystallized from 100% ethanol to give 2.10 g of [1-(2-methyl-4-phenyl)indenyl]-[-9-(1,2,3,4-tetrahydrofluorenyl)]dimethylsilane (50%).

The compound was an oily solid that did not display a true melting point. $^1$H NMR (CDCl$_3$): δ 7.57–7.11 (m, 12H, arom), 6.78 (bs, 1H Ind-C$_5$-sp$^2$), 3.77 (bs, 1H, Ind-C$_5$-sp$^3$), 3.63 (bs, 1H, THFlu-C$_5$-sp$^3$), 2.54–2.42 (m, 4 H, CH$_2$), 2.20–2.17 (d, 3H, CH$_3$), 1.95–1.55 (m, 4H, CH$_2$) , -0.26 (s, 3H, Si—CH$_3$), -0.27 (s, 3H, Si—CH$_3$). HRMS m/z for C$_{31}$H$_{32}$Si Calcd: 432.2273, Found: 432.2253.

b) Production of the Dilithium Salt

To a solution of 0.50 g (1.16 mmol) of [1-(2-methyl-4-phenyl)indenyl]-[-9-(1,2,3,4-tetrahydrofluorenyl)]dimethylsilane in 20 ml of dry diethylether at 0° C. was added dropwise two equivalents of a 1.6 M solution of butyllithium in hexane (1.45 ml, 2.32 mmol). The resulting suspension was stirred for 6 h at room temperature. The solvent was removed under vacuum and the residue was washed twice with 10 ml of dry pentane, giving a yellow solid.

c) Production of Dimethylsilylene-[$\eta^5$-1-(2-methyl-4-phenyl)indenyl]-[$\eta^5$-9-(1,2,3,4-tetrahydrofluorenyl)] Zirconium Dichloride The yellow solid obtained in (b) was suspended in 20 ml of dry diethylether and cooled to 0° C. Zirconium tetrachloride (0.27 g, 1.16 mmol) was added as a solid. The orange suspension was stirred overnight at room temperature and the solvent was removed by filtration. The residue was extracted with dry methylene chloride. The solution was concentrated and stored at −20° C. to give 290 mg of dimethylsilylene-[$\eta^5$-1-(2-methyl-4-phenyl)indenyl]-[$\eta^5$-9-(1,2,3,4-tetrahydrofluorenyl)] zirconium dichloride, an orange solid (42.2%), as a mixture of isomers (ca. 9:1). $^1$H NMR (CDCl$_3$): δ 7.65–6.90 (m, 12H, arom), 6.89 (s, 1H, Ind-C$_5$-sp$^2$), 3.04–2.55 (m, 4H, CH$_2$), 2.34 minor, 2.23 major (s, 3H, CH$_3$), 1.90–1.35 (m, 4H, CH$_2$), 1.46 minor, 1.31–1.29 major, 1.19 minor (s, 6H, Si—CH$_3$). HRMS m/z for C$_{31}$H$_{30}$SiCl$_2$Zr: Calcd: 590.0541, Found: 590.0535.

EXAMPLE 2

Preparation of the Dimethylsilylene-[$\eta^5$-1-(2-methyl-4-phenyl)indenyl]-[$\eta^5$-9-(1,2,3,4,5,6,7,8-octahydrofluorenyl)] Zirconium Dichloride (Catalyst 2).

a') Production of [1-(2-methyl-4-phenyl)indenyl]-[-9-(1,2,3,4,5,6,7,8-octahydrofluorenyl)] Dimethylsilane.

To a solution of 1.55 g (7.51 mmol) of 2-methyl-7-phenylindene in 30 ml of dry diethyl ether at 0° C. was added dropwise a 1.6 M solution of butyllithium in hexane (4.68 ml, 7.51 mmol). The solution was stirred at room temperature for 5 h. The solvent was removed under vacuum and the residue was washed twice with 20 ml of dry pentane.

The 2-methyl-7-phenylindenyllithium was dried under vacuum, dissolved in 30 ml of dry diethyl ether and 5 ml of dry THF and then added dropwise to 2.00 g (7.51 mmol) of 9-(chlorodimethylsilyl)-1,2,3,4,5,6,7,8-octahydrofluorene (prepared according to the method described by Marks et al., Organometallics, 1997, 16, 2503) in 20 ml of dry diethyl ether at −78° C. The mixture was allowed to warm to room temperature and stirred overnight to give a yellow suspension which was hydrolyzed with aqueous NH$_4$Cl. The organic phase was separated and the aqueous layer was extracted with ether. The combined organic phases were dried (MgSO$_4$), filtered and the solvent was removed. The oily residue was crystallized from 100% ethanol to give 1.85 g of [1-(2-methyl-4-phenyl)indenyl]-[-9-(1,2,3,4,5,6,7,8-octahydrofluorenyl)] dimethylsilane (56%). The compound was an oily solid that did not display a true melting point. $^1$H NMR (CDCl$_3$): δ 7.52–7.15 (m, 8H, arom), 6.79 (s, 1H Ind-C$_5$-sp$^2$), 3.74 (s, 1H, Ind-C$_5$-sp$^3$), 3.18 (bs, 1H, OHFlu-C$_5$-sp$^3$), 2.44–1.59 (m, 16H, CH$_2$), 2.22 (s, 3H, CH$_3$), –0.21 (s, 3H,Si—CH$_3$), –0.25 (s, 3H, Si—CH$_3$) HRMS m/z for C$_{31}$H$_{36}$Si: Calcd: 436.2586, Found: 436.2608.

b') Production of the Dilithium Salt and c') Production of Dimethylsilylene-[$\eta^5$-1-(2-methyl-4-phenyl)indenyl]-[$\eta^5$-9-(1,2,3,4,5,6,7,8-octahydrofluorenyl)] Zirconium Dichloride.

Following the procedure of steps b) to c) of example 1, using (0.50 g. 1.14 mmol) of [1-(2-methyl-4-phenyl)indenyl]-[-9-(1,2,3,4,5,6,7,8-octahydrofluorenyl)] dimethylsilane prepared in step a'), 1.6 M butyllithium in hexane (1.43 mL, 2.28 mmol) and ZrCl4 (0.27 g, 1.14 mmol) gave 310 mg of dimethylsilylene-[$\eta^5$-1-(2-methyl-4-phenyl) indenyl]-[$\eta^5$-9-(1,2,3,4,5,6,7,8-octahydrofluorenyl)] zirconium dichloride 45.6%) as a yellow solid. $^1$H NMR (CDCl$_3$): 7.74–7.02 (m, 8H, arom and 1H, Ind-C$_5$-sp$^2$), 2.76–1.20 (m, 16H, CH$_2$), 2.30 (s, 3H, CH$_3$), 1.17 (s, 3H, Si—CH$_3$), 1.05 (s, 3H, Si—CH$_3$). HRMS m/z for C$_{31}$H$_{34}$Cl$_2$SiZr: Calcd: 594.0854, Found: 594.0829.

2. Polymerization of Olefins

General Conditions

A 250 ml crown capped glass pressure reactor containing 50 ml of toluene was equilibrated with the appropriate monomer at the desired temperature and pressure. The desired amount of methylaluminoxane (MAO) was added as a solution in toluene via syringe, and the solution was stirred for 5 min. 1 ml of the appropriate metallocene catalyst solution in toluene was added and the mixture was stirred until the desired reaction time was reached. The mixture was quenched with 2% HCl in methanol, filtered (or extracted in the case of atactic polypropylene), and dried in a vacuum oven at an appropriate temperature for the polymer sample.

EXAMPLES 3 AND 4

These examples are related to the polymerization of ethylene under the general conditions described hereabove by using respectively catalyst 1 and catalyst 2 prepared in examples 1 and 2 respectively. The conditions are as follows:

Zr=5 $\mu$M, Al/Zr=4000:1 (atomic ratio), monomer pressure=15 psi

The duration of the polymerization was 6 min, the temperature was 50° C. The yield was 0.59 g for catalyst 1 (activity: 8.6×10$^7$ g polymer/(mol Zr.[ethylene]. h) (with [ethylene]=ethylene concentration in mol/l) and 0.65 g for catalyst 2 (activity: 9.5×10$^7$ g polymer/(mol Zr.[ethylene]. h).

COMPARATIVE EXAMPLE 5

Example 1 was repeated but the dimethylsilylene-(9-fluorenyl)-1-(2-methyl-4-phenyl)indenyl zirconium dichloride, preactivated for 10 minutes with 1 ml of MAO (catalyst 3), was used as catalyst.

The yield was 0.54 g (activity: 7.9×10$^7$ g polymer/(mol Zr.[ethylene]. h).

EXAMPLES 6 TO 9

These examples are related to propylene solution polymerization in toluene according to the general procedure described hereabove using the catalysts described in examples 1 and 2 respectively. The conditions are as follows:

Zr=25 $\mu$M, Al/Zr=4000:1 (atomic ratio), monomer pressure=30 psi.

The duration of the polymerization was 60 minutes, and the temperature was 20° C. or 70° C.

The results are listed in Table 1. The activity is expressed in g polypropylene/(mol Zr.[propylene].h) (with [propylene]=propylene concentration in mol/l).

TABLE 1

| Example | Catalyst | Temp (° C.) | Yield (g) | Activity | Tm (° C.) | mmmm |
|---|---|---|---|---|---|---|
| 6 | 1 | 20 | 18.0 | 1.40 × 10$^7$ | 118 | 84 |
| 7 | 1 | 70 | 16.0 | 9.00 × 10$^7$ | None | 49 |
| 8 | 2 | 20 | 6.5 | 0.52 × 10$^7$ | 138 | 87 |
| 9 | 2 | 70 | 11.3 | 6.40 × 10$^7$ | 81 | 56 |

TABLE 1-continued

| Example | Catalyst | Temp (° C.) | Yield (g) | Activity | Tm (° C.) | mmmm |
|---|---|---|---|---|---|---|
| 10R | 3 | 20 | 0.7 | 0.06 × 10$^7$ | 137 | 91 |
| 11R | 3 | 70 | 0.8 | 0.43 × 10$^7$ | 135 | 89 |

COMPARATIVE EXAMPLE 10R

Example 6 was repeated, but using catalyst 3. The results are shown in table 1.

COMPARATIVE EXAMPLE 11R

Example 7 was repeated, but using catalyst 3. The results are shown in table 1.

EXAMPLES 12 AND 13

These examples are related to the polymerization of ethylene using the catalysts described in examples 1 and 2. The polymerization conditions are as follows: Zr=2 $\mu$mol, in precontact with 2 ml MAO (10% by weight in toluene); monomer partial pressure=10 bars (solvent=hexane), MAO is used in a ratio Al/Zr of 15000:1, polymerization temperature=70° C., duration=1 h. The activity of the catalyst is expressed in g of polyethylene/mol Zr*hour.

The results of these tests are given in table 2 below.

TABLE 2

| Example | Catalyst | Temp. (° C.) | Yield (g) | Activity | Tm (° C.) |
|---|---|---|---|---|---|
| 12 | 1 | 70 | 185 | 9.25 × 10$^7$ | 129 |
| 13 | 2 | 70 | 245 | 12.25 × 10$^7$ | 115 |
| 14R | 3 | 70 | 82 | 8.20 × 10$^7$ | — |

COMPARATIVE EXAMPLE 14R

Example 12 was repeated but using 1 $\mu$mol of catalyst 3 in precontact with 1 ml of MAO, and isobutane as solvent. The results are reported in table 2.

EXAMPLE 15 AND 16

These examples are related to propylene bulk polymerization with catalyst 1 and 2 according to the following general procedure: the polymerization run is carried out in a 5 liter stainless steel reactor. Cocatalyst (MAO, 10% by weight in toluene, 45 ml), catalyst (5 $\mu$mol Zr in precontact with 5 ml MAO, 10% by weight in toluene), Al/Zr=15,000:1 (molar ratio), and liquid propylene (3.5 liters) are successively introduced under argon blanket and heated to the polymerization temperature (70° C.). The polymerization conditions are maintained for 60 minutes. The polymerization is then stopped by simultaneously flashing the residual monomer and cooling down the reactor.

The results of the polymerization trials are shown in table 3 below. The activity of the catalyst is expressed in g of polypropylene/mol Zr*hour.

TABLE 3

| Ex. | Catalyst | Temp. (° C.) | Yield (g) | Activity | Tm (° C.) | mm | Mw (daltons) | Mw |
|---|---|---|---|---|---|---|---|---|
| 15 | 1 | 70 | 309 | 6.18 × 10$^7$ | 139.7 | 85 | 16000 | 2.6 |
| 16 | 2 | 70 | 529 | 10.58 × 10$^7$ | 125.9 | 91 | 27000 | 1.9 |

What is claimed is:

1. Novel asymmetric silicon-bridged metallocenes useful as catalysts in the polymerization of olefins represented by the general formula (I):

$$(SiR'R'')(C_p)(C_{p'})MXX' \quad (I)$$

wherein $C_p$ is a partially or fully hydrogenated fluorenyl moiety selected from those of formula (II) and (III)

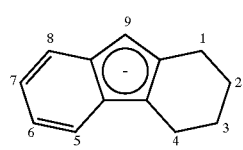

(II)

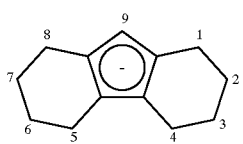

(III)

$C_{p'}$ is an indenyl group selected from those of formula (IV)

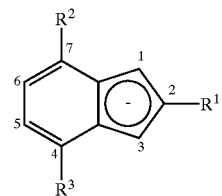

(IV)

M represents Zr,

X and X' each represent a chlorine atom, $R^1$, $R^2$ and $R^3$ are, same or different from each other, and selected from the group consisting of methyl, aryl of 6 to 10 carbon atoms and hydrogen, wherein at least one of $R^2$ and $R^3$ is other than hydrogen;

(SiR'R'') is a divalent group which bridges the two groups $C_p$ and $C_{p'}$ repectively on position 9 and 1, R' and R'' are, same or different from each other, an alkyl or aryl group containing from 1 to 10 carbon atoms.

2. Novel asymmetric silicon-bridged metallocenes according to claim 1 wherein R' and R'' are both methyl groups.

3. A novel asymmetric silicon-bridged metallocene according to claim 1, which is dimethylsilylene-[$\eta^5$-1-(2-methyl-4-phenyl)indenyl]-[$\eta^5$-9-(1,2,3,4-tetrahydrofluorenyl)] zirconium dichloride.

4. A novel asymmetric silicon-bridged metallocene according to claim 1, which is dimethylsilylene-[$\eta^5$-1-(2-methyl-4-phenyl)indenyl]-[$\eta^5$-9-(1,2,3,4,5,6,7,8-octahydrofluorenyl)] zirconium dichloride.

5. Process for the polymerization of α-olefins by means of the metallocenes according to claim 1.

6. Process according to claim 5 applied to the polymerization of ethylene or propylene.

* * * * *